(12) United States Patent
Chess et al.

(10) Patent No.: US 6,475,211 B2
(45) Date of Patent: *Nov. 5, 2002

(54) METHOD AND APPARATUS FOR TEMPERATURE CONTROL OF BIOLOGIC TISSUE WITH SIMULTANEOUS IRRADIATION

(75) Inventors: Cyrus Chess, Weston, CT (US); Michael L. Barretti, Westborough, MA (US)

(73) Assignee: Cool Laser Optics, Inc., Westborough, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/099,661

(22) Filed: Jun. 17, 1998

(65) Prior Publication Data

US 2001/0018603 A1 Aug. 30, 2001

Related U.S. Application Data

(60) Provisional application No. 60/549,858, filed on Jun. 17, 1997.

(51) Int. Cl.$^7$ ............................................... A61B 18/18
(52) U.S. Cl. .................. 606/9; 606/20; 606/2; 128/898
(58) Field of Search ............................. 606/9, 2, 10, 11, 606/12, 13, 20, 22, 24; 607/88, 89, 96, 104

(56) References Cited

U.S. PATENT DOCUMENTS

| | | | | |
|---|---|---|---|---|
| 4,313,093 A | * | 1/1982 | Suenaga et al. ............ | 372/109 |
| 4,733,660 A | * | 3/1988 | Itzkan ............................ | 606/9 |
| 5,057,104 A | | 10/1991 | Chess ............................. | 606/9 |
| 5,077,980 A | | 1/1992 | Weber ........................... | 62/130 |
| 5,282,797 A | | 2/1994 | Chess ............................. | 606/9 |
| 5,350,417 A | * | 9/1994 | Augustine ................... | 607/104 |
| 5,486,172 A | | 1/1996 | Chess ........................... | 606/20 |
| 5,520,679 A | * | 5/1996 | Lin ................................ | 606/5 |
| 5,554,172 A | * | 9/1996 | Horner et al. ................ | 607/88 |
| 5,570,706 A | * | 11/1996 | Howell ........................ | 128/898 |
| 5,630,811 A | | 5/1997 | Miller ........................... | 606/9 |
| 5,814,040 A | * | 9/1998 | Nelson et al. ................ | 606/9 |
| 5,849,029 A | * | 12/1998 | Eckhouse et al. ........... | 607/104 |
| 5,944,748 A | * | 8/1999 | Mager et al. ................ | 607/88 |
| 5,951,542 A | * | 9/1999 | Daikuzono .................... | 606/9 |
| 5,968,033 A | * | 10/1999 | Fuller et al. .................. | 606/9 |
| 5,979,454 A | * | 11/1999 | Anvari et al. ............... | 128/898 |
| 5,980,512 A | * | 11/1999 | Silberg ......................... | 606/9 |
| 6,214,034 B1 | * | 4/2001 | Azar ............................ | 607/89 |

FOREIGN PATENT DOCUMENTS

WO    WO97/15236    5/1997

OTHER PUBLICATIONS

"Erbium Laser Ablation of Dental Hard Tissue: Effect of Water Cooling" as appeared in *Lasers in Surgery and Medicine*; 18:294–300 (1996); by Steven R. Visuri et al.; pp. 294–300.

(List continued on next page.)

*Primary Examiner*—Rosiland S. Kearney
(74) *Attorney, Agent, or Firm*—Ohlandt, Greeley, Ruggiero & Perle, LLP (57) ABSTRACT

A method and apparatus for treatment of the skin or other biologic tissue includes the ability to subject said skin or other tissue to temperature modulation and radiation, simultaneously. The apparatus that delivers warm or cold material to the treatment site to effect this modulation of temperature may be attached to the apparatus that delivers radiation or it may be a separate entity, that could be utilized with a variety of radiation generating equipment.

24 Claims, 5 Drawing Sheets

OTHER PUBLICATIONS

"Laser Irradiation of Biological Tissue Through Water as a Means of Reducing Thermal Damage" as appeared in *Lasers in Surgery and Medicine*; 19:407–412 (1996); by Arieh Shalhav, et al.; pp. 407–412.

Candela Corporation Precision Series Product Sheet—"The Candela Dynamic Cooling Device", 2 pages.
Product sheet entitled "ARTX Stainless Steel Vortex Tubes" by ARTX Air Line, 4 pages.

* cited by examiner

METHOD AND APPARATUS FOR TEMPERATURE CONTROL OF BIOLOGIC TISSUE WITH SIMULTANEOUS IRRADIATION

This application claims the benefit of Provisional application Ser. No 60/049,858, filed Jun. 17, 1997.

FIELD OF THE INVENTION

The present invention relates generally to a method and apparatus that allows an area of biologic tissue such as the skin to be affected by alteration of its normal temperature,, and by a variety of different kinds of radiation. The method and apparatus allow these effects of temperature change and irradiation to occur simultaneously.

BACKGROUND OF INVENTION

Radiation from various portions of the spectrum is currently utilized in the treatment of a variety of skin conditions. Lasers, intense pulsed light. sources and other radiation emitting devices have been used to treat conditions including birthmarks, tattoos, benign vascular lesions, pigmented lesions, scars, warts, stria distensae, wrinkles and other benign or malignant skin lesions. Lasers and other light sources are also currently used for the removal of unwanted hair on various parts of the body.

For some of these conditions, cooling of the skin is used adjuctively to the delivery of light. Cooling is accomplished in a variety of ways. Cooling is used to reduce side effects and discomfort associated with the delivery of light in the above mentioned clinical situations. Some cooling of the skin is accomplished by the use of cold packs, or ice before and/or after light is delivered to the treatment site. Simultaneous cooling and lasing is currently accomplished by several methods.

One method of simultaneous cooling and lasing (Cool Laser Optics, Coherent Versapulse, Palomar Epitouch, Light Shear, Chill-Tip) utilizes an apparatus that subjects the treatment site to cooling delivered by a lens that is substantially transparent to the wavelength of light to be delivered to the skin. The lens must be in contact with the treatment site. This same lens is made cold by having a recirculating coolant contact an aspect of the lens other than the lens surface contacting the treatment site. A similar apparatus is used where the coolant does not recirculate, but rather is kept cool by ice that is held within the apparatus. Another apparatus sprays coolant at the lens. An index matching gel is sometimes used between the cooling lens and the surface being treated.

A problem with contact lens apparatus is an inability to make good skin contact on concave aspects of the skin surface. Although some contact cooling units have a flexible contact surface, certain areas of the skin, such as naso-ocular angle still cannot be contacted adequately. Another problem is that the lens is substantially transparent to the light being delivered. The lenses are commonly made of quartz glass or sapphire to maximize thermal conductance.

The pulsed spray cooling of the Dynamic Cooling Device (DCD) needs no contact with the treatment surface, but has other problems. DCD uses volatile liquid to spray at the skin. These substances may, or may not, have some hazard potential for the environment or for individuals inhaling these vapors. Whether these concerns are valid will require long term evaluation, and due to these concerns DCD will not be considered suitable or appropriate for some practitioners and patients.

In some instances, pre-cooled transparent gels are applied for similar purposes as stated above but without any method for maintaining a cool temperature of the gel after application to the skin.

Another kind of cooling utilizes a sprayed cryogenic liquid (dynamic cooling). The cryogenic liquid is sprayed at the treatment site just before the laser light is delivered to the skin. Evaporation of the sprayed cryogenic liquid cools the skin's surface.

Cryogenic liquids used with DCD may cause technical problems due to frosting or icing in the delivery system. Furthermore, very exact timing is necessary with DCD to achieve the desired cooling without interfering with the transmittance of light through vaporizing sprayed cryogenic liquid or frosting of the skin. This exact timing as well as the exact quantity of. cryogenic liquid sprayed is microprocessor controlled, and any alteration due to suboptimal functioning could reduce or eliminate the benefit of treatment or cause unanticipated injury.

These various methods of cooling are utilized in an expanding list of laser amenable conditions. Specifically, contact cooling units with a cooling lens component were originally designed for use with laser treatment for lower extremity telangiectasia. These cooling units are now also used with laser treatment for other benign vascular lesions, such as port wine birthmarks, and also for laser removal of hair. Similarly, the spray cooling units are utilized for treating vascular lesions and for hair. removal. Additionally, contact and spray cooling are used for laser treatment of facial wrinkles.

All of the above apparatus and techniques are used to cool tissues. None allow the treatment site to be warmed.

There are lasers (Erbium YAG) that cause debris to be scattered during treatment. Some of these lasers have air flow directed through and out of the end of the laser hand piece. The purpose of this air flow is to prevent debris from entering the laser hand piece and clouding the laser optics inside the hand piece. The temperature of this air flow is not controlled nor is its purpose to modulate the temperature of the treatment site.

SUMMARY OF THE INVENTION

Against the forgoing background it is a primary object of the present invention to enhance the ability to alter the temperature of the skin during laser or other irradiation of the skin. Existing technology only has the ability to reduce the skin's temperature.

It is another object of the present invention to allow heating of the skin during laser irradiation or alternatively to allow cooling.

It is still another object of the present invention to provide heating and/or cooling of the skin without making contact with the skin.

It is yet another object of the present invention to vary the temperature of the skin up or down depending on what kind of radiation is being utilized, and what condition is being treated.

Simply from the standpoint of simultaneous cooling and lasing the present invention has the additional object of avoiding problems that exist with the current cooling modalities that were mentioned above.

A further object of the present invention is to deliver warm or cool air to the skin surface without any potential for environmental or personal hazard.

It is an additional object of the present invention to avoid the use of complex technology in the delivery of a cooling medium to the treatment site so as to minimize cost to the user and maximize reliability, efficiency, and safety.

BRIEF DESCRIPTION OF DRAWINGS

Other and further objects, advantages and features of the present invention will be understood by reference to the following specification in conjunction with the accompanying drawings, in which like reference characters denote like elements of structure and.

DESCRIPTION OF PREFERRED EMBODIMENTS

The present invention provides apparatus and a method for treatment of biologic tissue that alters the temperature of the tissue either by cooling or by heating or by both while the tissue is being irradiated.

The benefits attributed to cooling laser treatment sites relate to decreased pain and side effects caused by the heat produced by certain high power laser systems or non laser light sources.

The benefits resulting from heating the treatment site include increased blood flow and the ability to reduce the amount of laser power needed. By reducing laser power less side effects result.

Figure 1:
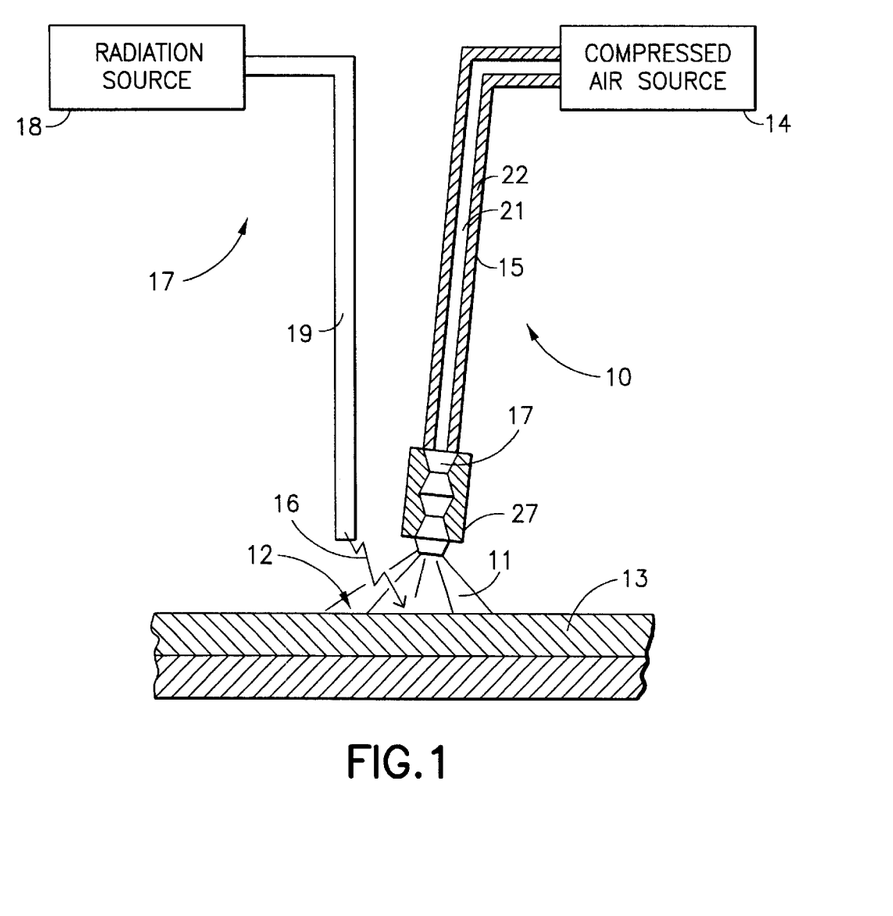
FIG. 1 is an elevational view in part and a cross sectional view in part of the temperature modulating device according to the present invention.

With reference to the drawings and, in particular, to FIG. 1, there is provided an apparatus generally represented by reference numeral 10 that delivers a temperature controlled medium 11 to a treatment site 12 of biologic tissue 13. Apparatus 10 includes a source 14 that delivers medium 11 via a delivery device 15 to treatment site 12. The temperature of medium 11 is controlled to be above or below the normal temperature of the biological tissue during irradiation of treatment site 12 by radiation 16.

Radiation 16 is provided from a radiation tool generally designated by reference numeral 17. Radiation tool 17 includes a radiation source 18 that delivers radiation 16 via a delivery device 19.

Although the present invention contemplates the use of any type of radiation that is useable to treat biologic tissue, the invention will be described herein where source 18 is a laser. For laser embodiments, delivery device 19 may comprise tubing such as fiber optic cable or other suitable conveyor of laser radiation.

The present invention also contemplates that medium 11 may be any suitable medium in liquid or gas state that can be controlled to warm and/or cool the temperature of the biologic tissue 13 above or below its normal temperature. Also, medium 11 is transparent to radiation 16. In the preferred embodiment, medium 11 is air and source 14 is shown as a source of compressed air.

The temperature and/or flow rate of air 11 are controlled by means situated either at compressed air source 14 or at any suitable location along its flow toward treatment site 12. In a preferred embodiment, the flow rate is controlled at air source 14 and the temperature is controlled by means of a vortex tube 20.

Delivery device 15 is connected at its proximal end to air source 14 by means of a suitable coupler such as a quick connect/disconnect device (not shown). Delivery-device 15 has a delivery tube 21 that is covered by an insulating material 22-made of similar material, running its entire length up to, but not including, vortex tube 20.

Figure 7:
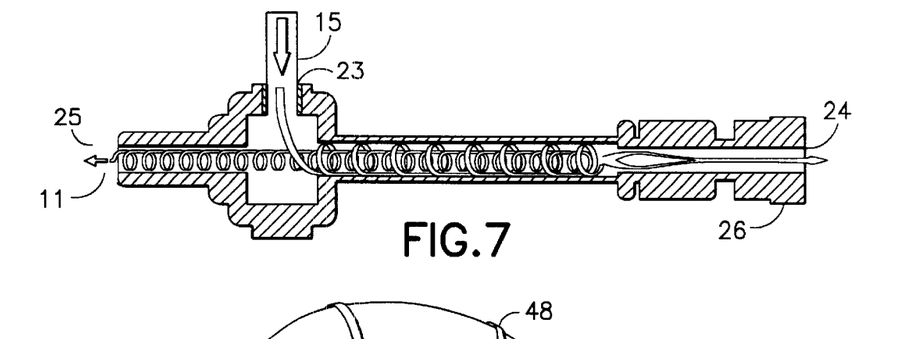
FIG. 7 is a cross sectional view of a vortex tube for the embodiments of FIGS. 1 through 6.

Vortex tube 20 controls the temperature of air 11 during its delivery. With reference to FIG. 7, vortex tube 20 typically has an inlet 23, a hot air vent 24 and an outlet 25 through which air 11 exits at a desired temperature. Inlet 23 is coupled to the distal end of delivery device 15 by plastic or polyurethane clamps or screw mounts (not shown). A manually adjustable valve 26 is situated at the hot air end of vortex tube 20 for control of the temperature of air 11 that exits outlet 25. Vortex tubes are available from The Air Research Technology Company of Fairfield, Ohio.

For the case of human skin tissue, the temperature of air 11 is in a range that controls the temperature of the biological tissue at treatment site 12 in a tissue temperature range that extends above and below the normal temperature of the tissue. For many clinical situations, the tissue temperature range will be from slightly above the freezing temperature of water and to about a high fever temperature, for example, about 32.5° F. to about 105° F. It is also contemplated that the temperature and/or flow of air may be controlled by valve 26 to be steady or variable during a treatment to accommodate clinical situations having different cooling and/or warming requirements. Depending on these modulating parameters and the heat transfer characteristics of air 11 as it moves from the point of control to treatment site 12, the actual temperature of the air 11 may vary from the above mentioned tissue temperature range.

A hand grip 27 preferably envelopes vortex tube 20. The enveloping is preferably from just above the distal end of hand grip 27 up to and including its proximal end and its connection to delivery device 15. Hand grip 27 permits manipulation of the direction of delivery device 15 as air 11 is delivered to the biologic tissue 13. Hand grip 27 is made of plastic, ASS, or anodized aluminum. In this embodiment, the vortex tube 20 is preferably directed at an angle that permits radiation 16 to pass through air 11 to treatment site 12. In this embodiment, the distal end of the vortex tube 20 is directed at an angle that permits the radiation 16 to pass through air 11 as it is delivered to the treatment site 12.

Delivery device 15 may be formed in a variety of lengths and diameters. In a preferred embodiment, delivery device 15 is about 12 feet long with an inside diameter of about ½ inch and an outside diameter of about ⅝ inch. It may be made from flexible polyurethane, or some other similar material. Vortex tube 17 is preferably flexible, but may be inflexible in some embodiments.

In other embodiments, vortex tube 17 may be omitted and the temperature of air 11 will be controlled by the source 14 or by a cooling or heating device (not shown) that is disposed between the source and treatment site 12.

Figure 8:
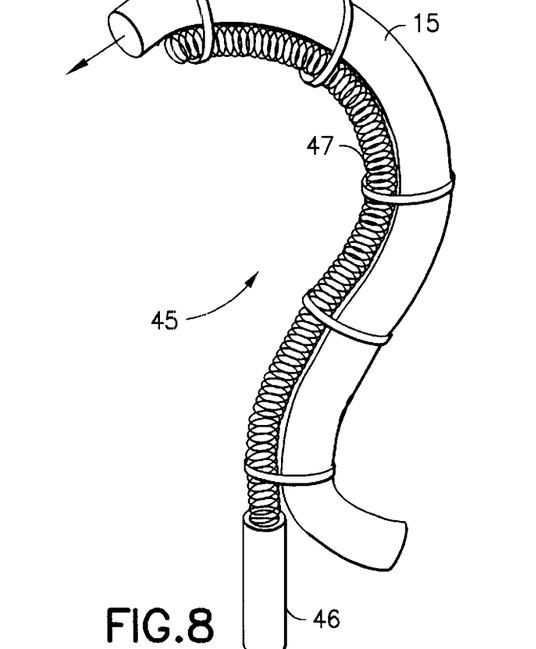
FIG. 8 is an elevational view of a semi-rigid stand useful with apparatus of FIG. 1.

Referring to FIG. 8, there is provided a semi-rigid stand 45 for holding delivery device 15 in a semi-rigid position. Stand 45 includes a rigid base 46 that is attached to a floor, wall, ceiling or portable structure that has some degree of rigidity. A semi-rigid gooseneck tubing 47 is attached to and extends from base 46. Delivery device 15 is attached to gooseneck tubing 47 by one or more clasps 48. The gooseneck tubing can be flexed with some exertion of force to move from one position to another. It is semi-rigid in the sense that it holds a position until such force is exerted. In operation, the gooseneck is positioned for delivery of air 11 to treatment site 12. This position is then held due to the semi-rigid nature of semi-rigid stand 45.

Figure 2:
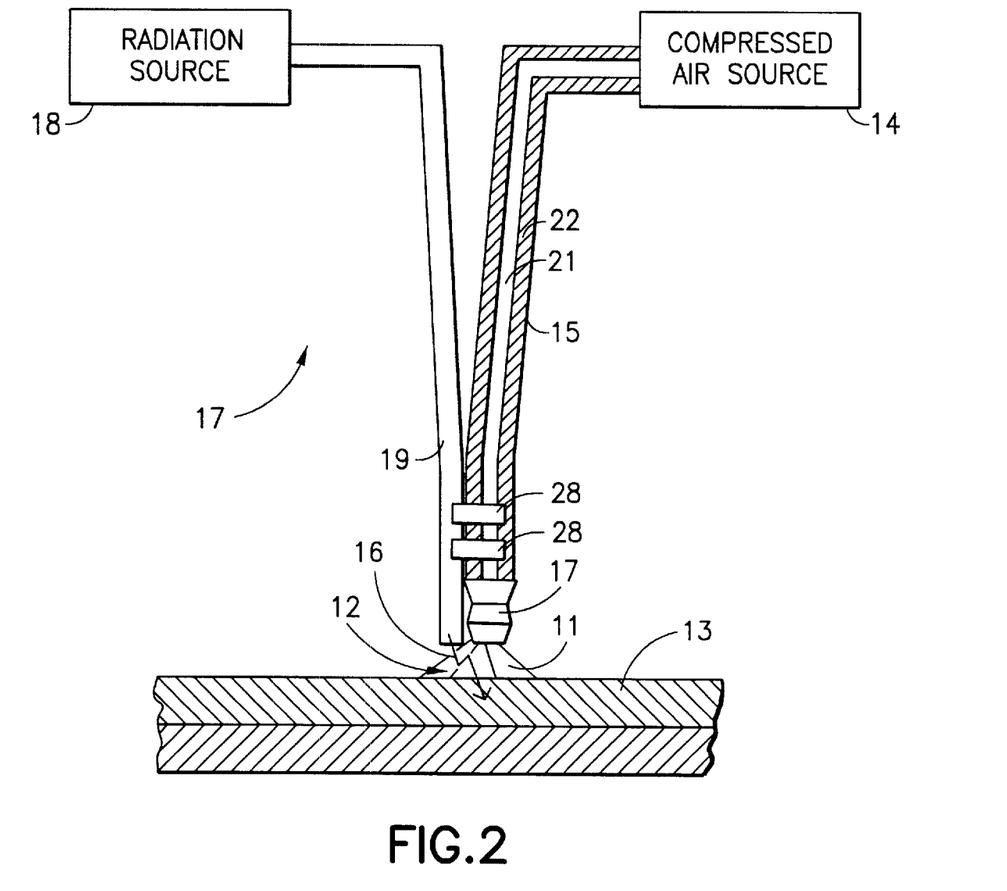
FIG. 2 is an elevational view in part and a cross sectional view in part of a combined temperature modulating device and radiation tool according to the present invention.

In another embodiment shown in FIG. 2, the distal end of air delivery device 15 is coupled to radiation delivery device 19 by clamps 28. The coupling is in a manner that permits manual manipulation of the direction of both the delivery device 15 of temperature modulation apparatus 10 and delivery device 19 of radiation tool 17 in concert with each other as they simultaneously deliver air 11 and radiation 16 to treatment site 12. Clamps 28 may be made of plastic, polyurethane or metal. In this embodiment, the distal end of the delivery device 15 is generally angled in such a manner as to permit radiation 16 to pass directly through air 11 being directed at treatment site 12.

Figure 3:
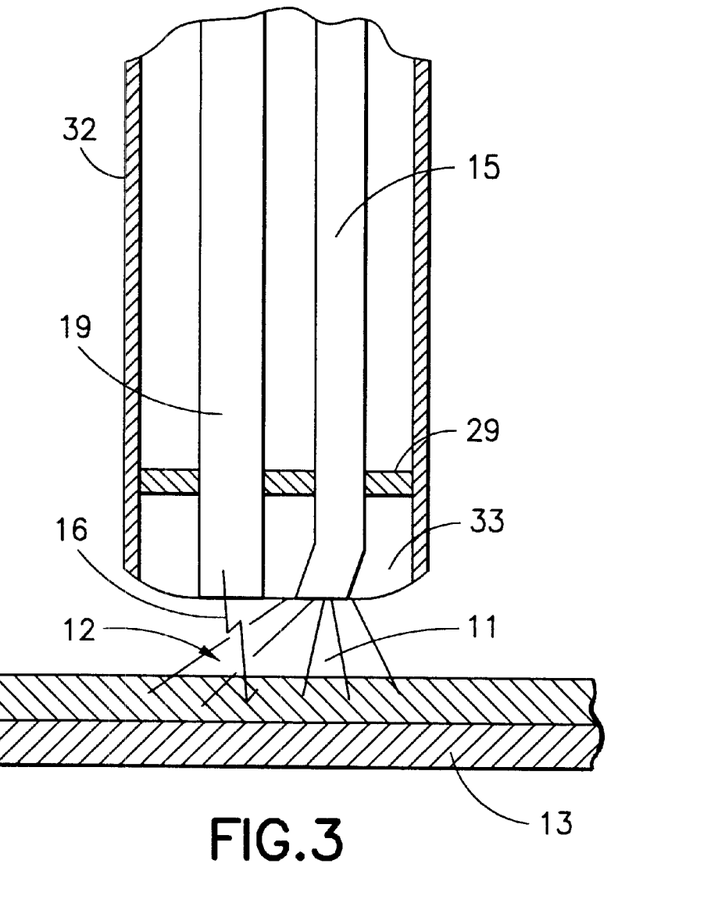
FIG. 3 is an elevational view in part and a cross sectional view in part of another embodiment of a combined temperature modulating device and radiation tool according to the present invention.
Figure 4:
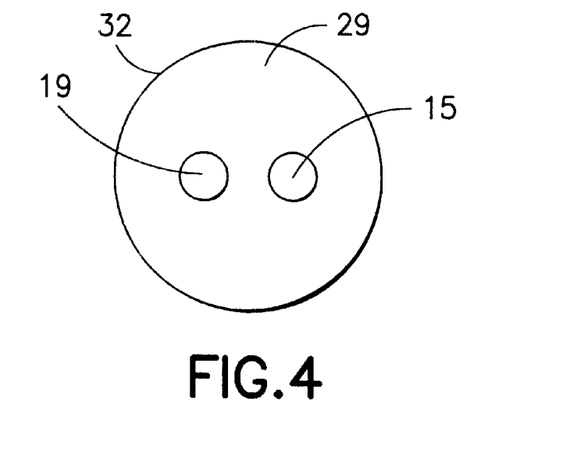
FIG. 4 is a top view of FIG. 3.

In another embodiment shown in FIGS. 3 and 4, a hand-held housing or hand piece 32 encases delivery devices 15 and 19 of apparatus 10 and radiation tool 17 in a generally parallel manner. This permits the simultaneous manual manipulation of both radiation delivery device 19 and air delivery device 15. In this embodiment, the distal end of air delivery device 15 is angled as indicated at 33 in a manner which permits radiation 16 to pass directly through the air 11 being delivered to biologic tissue 13. The housing 32 may be made of plastic or metal, or other similar material. A lens arrangement (not shown) may optionally be provided for the delivery of radiation 16 to treatment site 12. One or more spacers 29 are provided to hold delivery devices 15 and 19 in place within housing 32.

Figure 5:
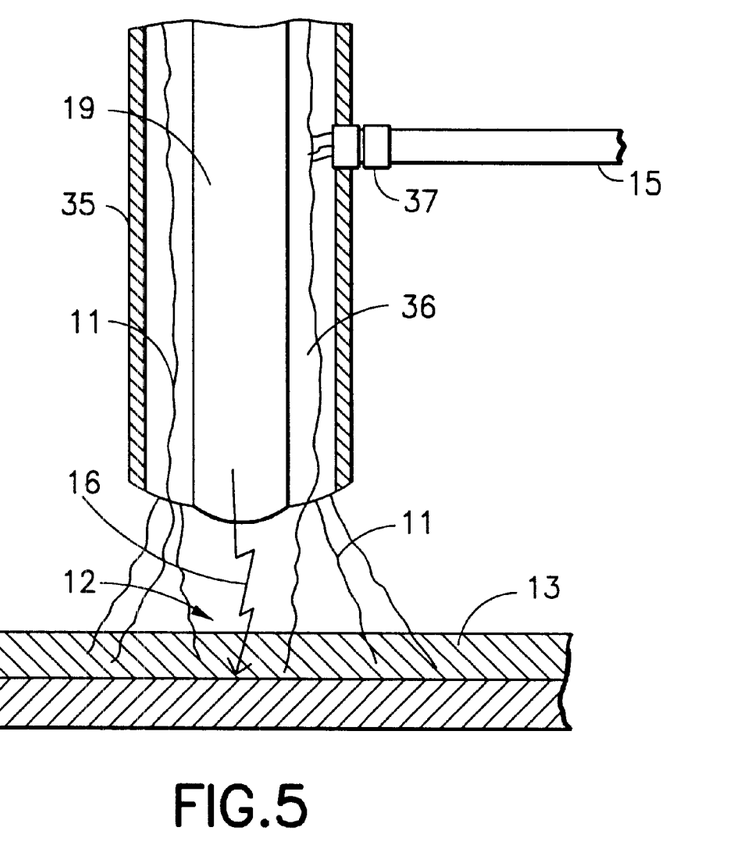
FIG. 5, is an elevational view in part and a cross sectional view in part of still another embodiment of a combined temperature modulating device and radiation tool according to the present invention.
Figure 6:
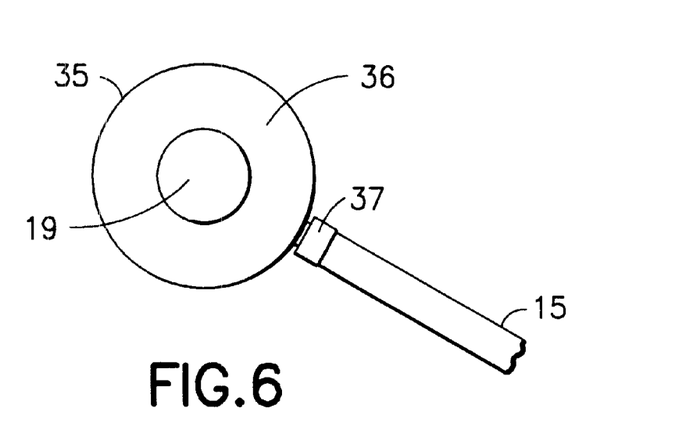
FIG. 6 is a top view of FIG. 5.

In another embodiment, shown in FIGS. 5 and 6, a hand-held housing or hand piece 35 encases the delivery device 19. Hand piece 35 includes a cylindrical or annular cavity 36 that surrounds delivery device 19. Spacers (not shown) may be provided to hold delivery device 19 in place within hand piece 35. The cooling or warming air 11 is introduced into cavity 36 from delivery device 15 via an in-line coupling 37 at the side of hand piece 35 or other suitable point. The in-line coupling 37 may be made of nylon or metal or other similar material. As air 11 is introduced into cavity 36, it completely surrounds the delivery device 19 and then exits at the distal end of hand piece 35 onto treatment site 12. The radiation 16 is simultaneously delivered by delivery device 19 through air 11 to treatment site 12.

Figure 9:
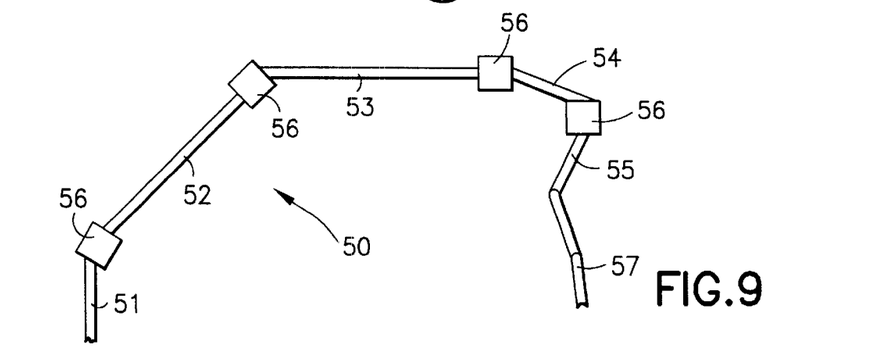
FIG. 9 is an elevational view of an articulated arm useful for delivery of radiation in the embodiments of FIGS. 1 through 6.

The delivery device 19 that conveys radiation 16 from radiation source 18 in the embodiments of FIGS. 1 through 6 may comprise tubing such as fiber optic cable or other suitable conveyor of laser radiation. Such cable or other conveyor may suitably be implemented in an articulated arm 50 shown in FIG. 9. Articulated arm 50 includes a base 51 that receives radiation from radiation source 18. The radiation is directed through a series of arm elements 52, 53, 54 and 55 to a laser hand piece 57. A set of knuckles 56 is provide to enclose mirrors or prisms that redirect the laser radiation from one arm element to the next in the series and joint that allow motion along one or more axes.

The method of the present invention involves delivering radiation to treatment site 12 of biologic tissue 13 and simultaneously delivering a temperature modifying medium to the treatment site. The temperature of the medium is controlled above and below the normal temperature of the tissue. The temperature of the medium can also be modulated during its delivery to the treatment site. Additionally, the flow rate of the medium can be controlled or adjusted.

The present invention having been thus described with particular reference to the preferred forms thereof, it will be obvious that various changes and modifications may be made therein without departing from the spirit and scope of the present invention as defined in the appended claims.

What is claimed is:

1. An apparatus for delivery of a temperature modifying medium to a treatment site of biologic tissue, coincident with the delivery of radiation to said treatment site, said apparatus comprising:

means for delivering a flow of said medium toward said treatment site; and means for controlling the temperature of said medium, said controlling means having the capability of controlling said temperature in a range that extends above or below the normal temperature of said treatment site.

2. The apparatus according to claim 1, wherein said delivery means includes a source of said medium and a delivery device for conveying said medium from said source to said treatment site.

3. The apparatus according to claim 2, wherein said delivery device includes tubing to convey said medium; and wherein said tubing is attached to a semi-rigid stand to maintain the direction of flow of said medium toward said treatment site.

4. The apparatus according to claim 1, wherein said medium is selected from the group consisting of liquid and gas.

5. The apparatus according to claim 1, wherein said medium is air.

6. The apparatus according to claim 1, further comprising:

means for controlling the flow rate of said medium to said treatment site, wherein said means for controlling said flow rate has the capability of maintaining said flow rate to be either steady or variable.

7. The apparatus according to claim 1, wherein said controlling means modulates said temperature of the medium during treatment of said treatment site.

8. An apparatus according to claim 1, wherein said temperature of said medium is controlled to provide a temperature at said treatment site that is in a range from slightly below freezing as well as above freezing to about a high fever temperature.

9. The apparatus according to claim 1, wherein said treatment site is topical.

10. An apparatus for delivering radiation and a temperature modifying medium simultaneously to a treatment site of biologic tissue, said apparatus comprising:

first and second delivery means for simultaneously delivering said radiation and said temperature modifying medium, respectively, to said treatment site;

means for controlling the temperature of said medium, said controlling means having the capability of controlling said temperature in a range that extends above and below the normal temperature of said treatment site; and means for connecting said first and second delivery means together to permit manual manipulation of the direction of said radiation and said medium flow in concert to said treatment site.

11. The apparatus according to claim 10, wherein said connecting means includes at least one clamp for clamping together said first and second delivery means.

12. The apparatus according to claim 10, wherein said connecting means includes a housing; and wherein said first and second delivery means are secured to said housing to permit manual manipulation of said housing to control the direction of said radiation and said medium flow in concert to said treatment site.

13. The apparatus according to claim 12, wherein said first and second delivery means are disposed within said housing.

14. The apparatus according to claim 13, wherein said first and second delivery means are secured to said housing by at least one spacer.

15. The apparatus according to claim 12, wherein said first delivery means is disposed within a cavity in said housing to deliver said radiation through an open end of said cavity to said treatment site; and wherein said second delivery means is disposed to deliver said medium into said cavity so that said medium flows adjacent said first delivery means and through said opening toward said treatment site.

16. The apparatus according to claim 15, wherein said first delivery means is tubing centrally disposed within said cavity and said medium flows in a space between said tubing and a wall of the cavity.

17. The apparatus according to claim 12, wherein said first delivery means comprises a fiber optic cable.

18. The apparatus according to claim 12, wherein said first delivery means is an articulated arm.

19. The apparatus according to claim 10, wherein said medium is transparent to the wavelength of a substantial amount of said radiation.

20. A method of treating a treatment site of biologic tissue that has a normal temperature, said method comprising:

delivering radiation to said treatment site;

simultaneously delivering a temperature modifying medium to said treatment site; and controlling the temperature of said medium in a range that extends above or below said normal temperature as said medium is being delivered to said treatment site.

21. The method according to claim 20, wherein said temperature of said medium is modulated by said controlling step as said medium is being delivered to said treatment site and wherein the temperature of said medium is controlled to warm and/or cool the biologic tissue of said treatment site.

22. The method of claim 21, further comprising:

controlling the flow rate of said medium as it is being delivered to said treatment site to be either steady or variable.

23. An apparatus for delivery of a temperature modifying medium to a treatment site of biologic tissue, coincident with the delivery of radiation to said treatment site, said apparatus comprising:

means for delivering a flow of said medium toward said treatment site; and means for controlling the temperature and flow rate of said medium, said controlling means having the capability of controlling said temperature in a range that extends above or below the normal temperature of said treatment site and of maintaining said flow rate either steady or variable.

24. The apparatus of claim 23, wherein said means for controlling includes an adjustable valve that adjusts said flow rate.

* * * * *